United States Patent [19]

Egger

[11] Patent Number: Plant 6,963

[45] Date of Patent: Aug. 1, 1989

[54] VERBENA PLANT CALLED VERBENA "A"

[75] Inventor: Janet N. Egger, Ventura, Calif.

[73] Assignee: Mitsuwa Nursery, Inc., Moonpark, Calif.

[21] Appl. No.: 203,016

[22] Filed: Jun. 6, 1988

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Roylance, Abrams, Berdo & Goodman

[57] ABSTRACT

A perennial hybrid Verbena groundcover called Verbena "A" which is particularly distinguished by the lavender pink color of its flowers, a color which was not heretofore known to exist in Verbena groundcovers. In addition, the invention plant is floriferous and shares many desirable qualities enjoyed by its parent plants.

1 Drawing Sheet

BACKGROUND TO THE INVENTION

The present invention relates to a new and distinctive cultivar of Verbena plant botanically known as Verbena hybrid and referred to commercially by the cultivar name, Verbena "A". Verbena "A" was developed by controlled breeding by crossing two commercial varieties, Verbena 'St. Paul' (seed parent) with *Verbena tenuisecta* hybrid (pollen parent).

BRIEF DESCRIPTION OF THE INVENTION

Verbena "A" is a perennial trailing groundcover with deep green leaves and floriferous, showy, lavender pink flowers that bloom year round in Southern California. The unique lavender pink color is believed to be a substantial step forward and an important advantage for Verbena "A" as compared to all other Verbena groundcovers.

DESCRIPTION OF THE DRAWING

The accompanying color photograph, forming a part of this disclosure, was taken in January 1988 in a greenhouse in Moorpark, Calif., and shows a close-up of Verbena "A" growing in a nursery flat the view being more or less straight down onto the plant. The photograph shows the typical flower and foliage form and color as true as is reasonably possible in this type of color photograph.

Comparison of Verbena "A" with its Parent Plants

The following characteristics distinguish Verbena "A" from its parents which are the only similar plants sold in the California groundcover industry.

The primary distinguishing characteristic of Verbena "A" is its lavender pink color. This color is new to Verbena groundcovers, that is, to the inventor's knowledge, Verbena "A" is the first such Verbena groundcover having flowers of this color. It is believed that its unique lavender pink color contributes substantially to the commercial success of Verbena "A".

In comparison to Verbena 'St. Paul', a common rose colored flowering groundcover, Verbena "A" is distinguished by having slightly smaller flowers, a larger number of flowers per spike, and leaves that are botanically described as being cut into linear divisions rather than lacerate. Verbena "A" has the excellent qualities of height, growth habit, disease resistance, bloom season, and vigor of its parent Verbena 'St. Paul'.

In comparison to *Verbena tenuisecta* hybrid, a common lavender-blue flowered groundcover, Verbena "A" is distinguished by having slightly larger pink flowers, a larger number of flowers per spike, smaller leaves, greater disease tolerance, lower height, and a more prostrate habit. Verbena "A" and *Verbena tenuisecta* are similar in their leaf type and bloom season.

DETAILED DESCRIPTION

The following is a detailed description of Verbena "A" based on plants produced under commercial practices outdoors at Mitsuwa Nursery, Inc., in Moorpark, Calif. Color references are made to The Royal Horticultural Society Colour Chart, except where the context indicates a term having its ordinary dictionary meaning.

Parentage: A controlled cross of Verbena St. Paul' as the seed parent and *Verbena tenuisecta* hybrid as the pollen parent.

Propagation: Asexual reproduction by stem cuttings has shown that the unique features of this new Verbena "A" are stable and are reproduced true to type in successive propagations. Verbena "A" roots rapidly under warm conditions due to its vigor. It also roots adventitiously at every node.

Plant form: Plants are a vigorous growing, trailing groundcover.

Habit of growth: Plants are decumbent, spreading rapidly to approximately 3 feet in diameter under good growing conditions. Plants for a dense carpet to approximately 1 foot in height.

Stems: Stems are slender, 4-angled, wine colored in the sun and green in the shade, and covered with strigose hairs.

Foliage: Foliage is a rich deep green with simple, opposite leaves.

(1) *Size.*—2–4 cm. in length.

(2) *Shape.*—Deltoid, 3-pinnatifid into linear entire divisions, with an attenuate base and acute segment apices.

(3) *Texture.*—Covered with white strigose hairs.

(4) *Margin.*—Subrevolute.

(5) *Color.*—Young foliage, top side — 137 A and B. Young foliage, underside — 137 C. Mature foliage, top side — 139 A. Mature foliage, underside — 147 B.

Flowering description:

(1) *Habit.*—Terminal spikes on ascending penducules which are dense and fairly flat when young but elongate when mature. Flowers on each spike continue to open for several weeks. Each spike has 40–96 flowers. Plants are very free flowering.

(2) *Season of bloom.*—varies with climate. In Moorpark, Calif., Verbena "A" flowers year round but heaviest bloom is in the warm season (March–October).

(3) *Flowers.*—Sessile on terminal spikes which are compact when young, but elongate to 11 cm. when mature. Each flower has a subtending lanceolate-subulate bract with strigose hairs.

(4) *Flower parts.*— (a) Corolla tube straight (11–12 mm) limb spreading (11–14 mm). (b) Calyx is tubular, sparsely glandular, with white strigose hairs and short teeth. It is more than twice as long as the bract. (c) Stamens: four, in pairs. The top pair with barely exerted black anther appendages.

(5) *Color of petals.*—New buds to just open flowers, inside — 84A. Mature flowers, upside — 81C and 82C. downside — 76A and 77D.

Disease resistance: No disease problems noted. Verbena "A" requires no fungicide drenching when grown under the propagation conditions of high heat and humidity, as are found in Moorpark, Calif.

I claim:

1. A new and distinct cultivar of Verbena as described and illustrated, particularly characterized by its floriferous showy lavender pink flowers, deep green foliage, vigorous growth, and trailing habit.

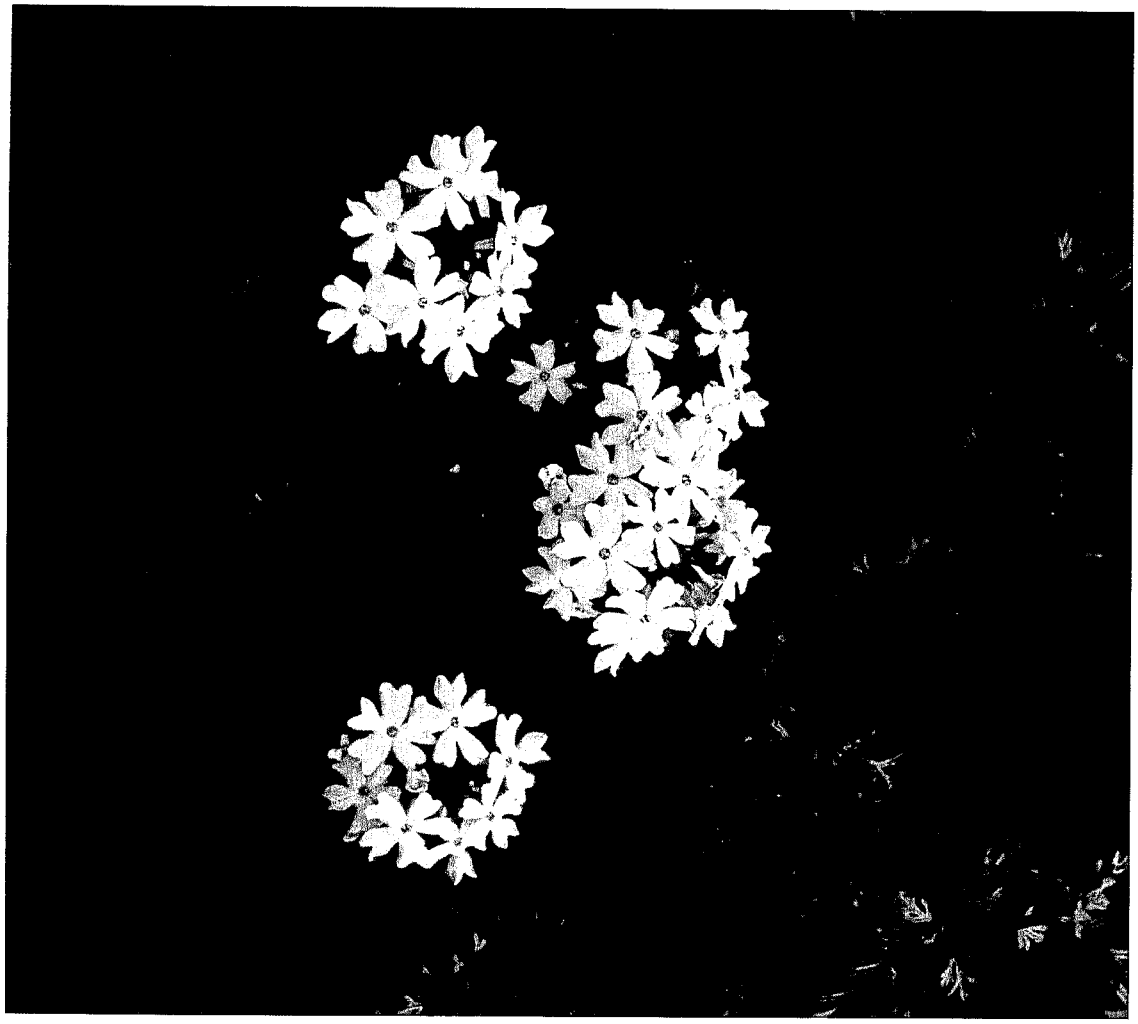

* * * * *